(12) United States Patent
Naegerl

(10) Patent No.: US 7,785,369 B2
(45) Date of Patent: Aug. 31, 2010

(54) ARTIFICIAL INTERVERTEBRAL DISK

(75) Inventor: Hans Naegerl, Gleichen (DE)

(73) Assignee: HJS Gelenk System GmbH, Munich (DE)

( * ) Notice: Subject to any disclaimer, the term of this patent is extended or adjusted under 35 U.S.C. 154(b) by 0 days.

(21) Appl. No.: 10/599,524

(22) PCT Filed: Mar. 3, 2005

(86) PCT No.: PCT/DE2005/000373
§ 371 (c)(1),
(2), (4) Date: Sep. 29, 2006

(87) PCT Pub. No.: WO2005/094734
PCT Pub. Date: Oct. 13, 2005

(65) Prior Publication Data
US 2007/0185579 A1 Aug. 9, 2007

(30) Foreign Application Priority Data
Mar. 30, 2004 (DE) ........................ 10 2004 016 032

(51) Int. Cl.
A61F 2/44 (2006.01)
(52) U.S. Cl. ............... 623/17.13; 623/17.11; 623/17.15
(58) Field of Classification Search ... 623/17.11–17.16; 606/61, 246
See application file for complete search history.

(56) References Cited

U.S. PATENT DOCUMENTS

| 3,867,728 | A | | 2/1975 | Stubstad et al. | |
|---|---|---|---|---|---|
| 5,071,437 | A | | 12/1991 | Steffee | |
| 5,401,269 | A | | 3/1995 | Buttner-Janz et al. | |
| 5,549,679 | A | | 8/1996 | Kuslich | |
| 5,571,189 | A | | 11/1996 | Kuslich | |
| 5,645,597 | A | | 7/1997 | Krapiva | |
| 5,824,094 | A | | 10/1998 | Serhan et al. | |
| 6,162,252 | A | | 12/2000 | Kuras et al. | |
| 6,368,350 | B1 | | 4/2002 | Erickson et al. | |
| 6,682,562 | B2 | * | 1/2004 | Viart et al. | 623/17.14 |
| 7,169,181 | B2 | * | 1/2007 | Kuras | 623/17.11 |
| 7,201,776 | B2 | * | 4/2007 | Ferree et al. | 623/17.16 |
| 2002/0035400 | A1 | * | 3/2002 | Bryan et al. | 623/17.15 |
| 2003/0009224 | A1 | | 1/2003 | Kuras | |
| 2003/0199982 | A1 | | 10/2003 | Bryan | |

(Continued)

FOREIGN PATENT DOCUMENTS

AU 2003291563 6/2004

(Continued)

Primary Examiner—Thomas C Barrett
Assistant Examiner—Andrew Yang
(74) Attorney, Agent, or Firm—Leydig, Voit & Mayer, Ltd.

(57) ABSTRACT

An artificial intervertebral disk, insertable between two adjacent vertebral bodies of a patient and joining the two adjacent vertebral bodies an articulated manner, includes an intermediate element embodied as an elastic ring and is inserted into one respective molded portion of two outer elements configured as metal plates. The outer elements are joined to the bones of the vertebral bodies via anchoring pins, especially titanium anchorings previously known in hip endoprosthetics. The radius of the concave molded portion is greater than the diameter of a circular cross-sectional area of the intermediate element such that compression of the intermediate element caused particularly by the patient's movement allows for a defined deformation.

12 Claims, 3 Drawing Sheets

U.S. PATENT DOCUMENTS

2005/0216081 A1*  9/2005  Taylor .................... 623/17.11

FOREIGN PATENT DOCUMENTS

| DE | 42 08 115 | 9/1993 |
| DE | 42 13 771 | 9/1993 |
| DE | 19710392 | 7/1999 |
| DE | 10024922 | 1/2002 |
| DE | 102 42 329 | 4/2004 |
| EP | 0 560 140 | 9/1993 |
| EP | 0 610 837 | 8/1994 |
| EP | 0747025 | 12/1996 |
| EP | 1041945 | 10/2000 |
| EP | 1 287 795 | 3/2003 |
| EP | 1 344 507 | 9/2003 |
| EP | 1 344 508 | 9/2003 |
| FR | 2 787 019 | 6/2000 |
| JP | 6007391 | 1/1994 |
| WO | WO-02/080818 | 10/2002 |
| WO | WO-02089701 | 11/2002 |
| WO | WO 03/063727 A2 | 8/2003 |

* cited by examiner

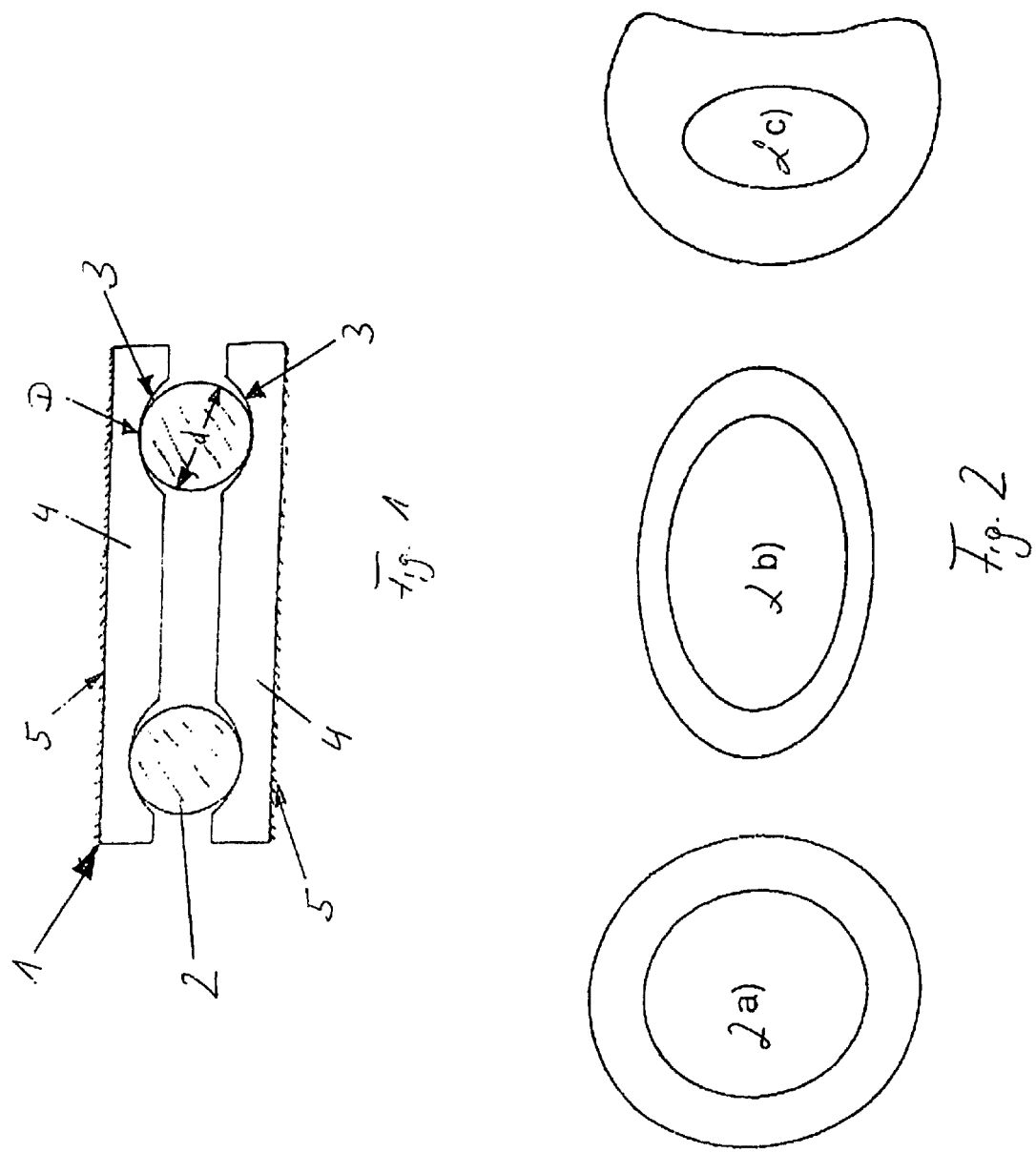

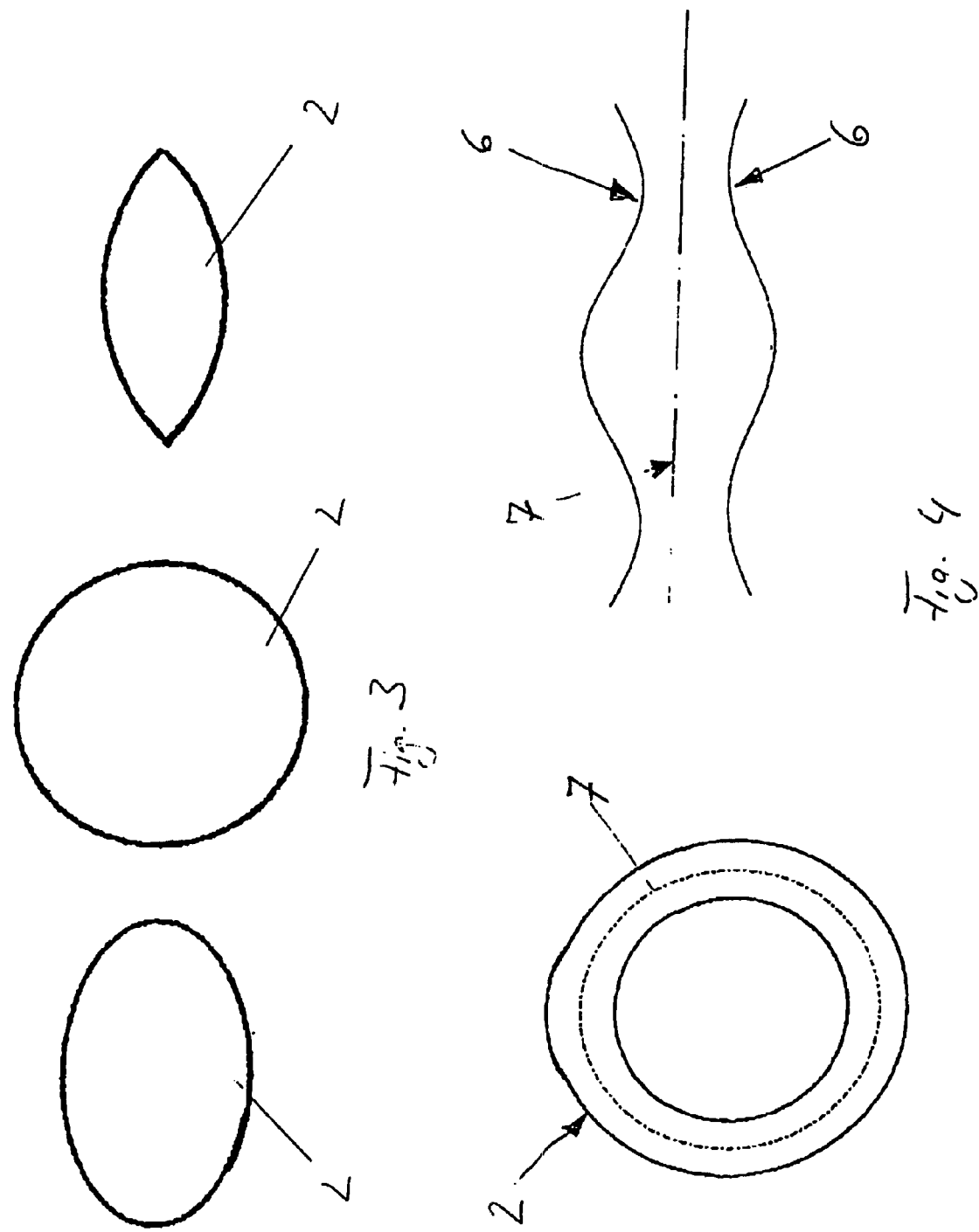

ARTIFICIAL INTERVERTEBRAL DISK

The present invention relates to an artificial intervertebral disk that can be inserted between two adjacent vertebral bodies of a patient, each artificial intervertebral disk having an element associated with the corresponding vertebral body, whereby the elements are joined to each other by means of an intermediate element in such a restricted, articulated manner that torsional moments as well as shear forces can be transmitted.

BACKGROUND

In the human vertebral column and especially in the lumbar vertebral column, the intervertebral disk (spinal disk) connects an upper osseous vertebral body in an articulated manner with a lower osseous vertebral body.

Such an artificial intervertebral disk is known, for example, from European patent application EP 0 610 837 B1 in which two plates are joined to each other by an elastomer core. The elastomer core has an upper part and a lower part that enclose an intermediate part whose peripheral surface is concave. In this manner, when bending moments or transmission forces are exerted onto the intervertebral disk, the forces generated on the contact surface between the plates and the core should be reduced in comparison to a core having straight sides.

U.S. Pat. No. 3,867,728 describes an intervertebral disk that consists, for example, of one single piece and that has a concave outer surface.

Moreover, U.S. Pat. No. 5,071,437 describes a spinal disk prosthesis comprising an upper flat plate, a lower flat plate, and a flat elastomeric core interposed between said plates.

EP 0 747 025 B 1 describes an artificial spinal disk for use between adjacent vertebrae, with a first component having a concave recess as well as a second component having a projection that fits into the recess of the first component so that an unrestricted tilt-and-turn movement is achieved between the first component and the second component.

Furthermore, DE 100 24 922 C1, EP 10 41 945 A1, WO 02/080818 A1, U.S. Pat. No. 6,368,350, DE 42 13 771 C1, EP 05 60 140 B1, EP 13 44 508 A1, EP 13 44 507 A1, DE 42 08 115 A1, EP 12 87 795 A1, DE 102 42 329 A1 and DE 197 10 392 C1 also disclose other spinal disk prostheses.

A drawback of all of the artificial intervertebral disks known so far is that the natural joint properties can only be insufficiently replicated. The patient clearly perceives this restriction of the natural range of motion as causing discomfort when several vertebral bodies have been replaced, as a result of which the disadvantageous properties of the intervertebral disks multiply.

SUMMARY OF THE INVENTION

An object of the present invention is to improve the properties of an artificial intervertebral disk that are perceptible to the patient.

Consequently, according to the invention, an artificial intervertebral disk is provided wherein the two elements have a contour by means of which the elements are joined to the intermediate element in a form-fitting manner. The invention is based on the notion that the desired range of motion can replicate the natural range of motion of the vertebral column in an optimal manner using an artificial intervertebral disk if the intermediate element is held positively in a corresponding contour of the element, since this means that torsional moments as well as shear forces can be transmitted without any problem and without having to forgo good deformation properties of the intervertebral disk. As a result, the intervertebral disk can be configured especially so that, at the same time, the relative mobility of the elements with respect to each other, that is to say, especially a tilting movement, can be greatly optimized, i.e. the mobility can be improved. In other words, when the function of the transmission of torsional moments and shear forces between adjacent vertebral bodies is uncoupled from the function of the articulated connection of the elements that are associated with the vertebral bodies —the latter function being uniformly achieved according to the state of the art by the elastic properties of the intermediate element in an inadequate manner as a compromise among the various properties —this uncoupling results in essentially divergent degrees of freedom corresponding to the optimum in each case. Thus, according to the invention, it is possible to join adjacent vertebral bodies in such an articulated manner that mechanical properties are attained that are similar to those of the natural intervertebral disk.

An especially advantageous embodiment of the vertebral disk according to the invention is achieved in that the contour is concave, thereby forming, for example, a recess for form-fit receiving the intermediate element. The contact surfaces are configured here in such a way that, in any case, the cohesive friction cannot be overcome by the shear and torsional load.

In actual practice, it has proven to be especially promising for the contour to have a friction-optimized surface texture, since as a result, any possible abrasion of the material of the intermediate element can be reduced or prevented in a simple manner. For example, in the contact area, the surfaces of the contour are polished with a specular finish in the contact area so that, when relative movements occur at the contact surfaces, the friction and thus also the abrasion on the intermediate element is minimal.

In contrast, another likewise practical modification is achieved if the contour has a surface texture or roughness that increases the friction, at least in sections, in order to create a frictional connection between the two elements and the intermediate element. In this manner, a design of the contact surfaces is achieved with which, in any case, the cohesive friction is not overcome by the shear and torsional load.

Moreover, it has proven to be especially practical for the contour to be configured with such an oversize with respect to the intermediate element that a compression of the intermediate element stemming especially from movement by the patient allows a defined deformation. Here, the surface curvature causes the contour to be dimensioned slightly smaller in comparison to the cross sectional surface of the intermediate element, so that the deformation of the intermediate element, which is, for example, annular, that occurs in response to compression allows its expansion parallel to the plane of the elements.

The intermediate element could be configured as a disk whose edge area has beads that engage in the correspondingly shaped contour. In contrast, an especially promising configuration is achieved if the intermediate element has an annular closed shape. In this manner, the torsional moments and shear forces that occur during movement can be transmitted in an optimal manner and, in addition to circular intermediate elements, it is also suitable to use oval or kidney-shaped intermediate elements since these already allow a form-fit transmission of torsional moments due to their basic shape, which diverges from the circular shape.

According to another likewise especially advantageous variant, the annular intermediate element has an ogival, oval or circular cross sectional surface crosswise to its annular central axis, at least in sections, so as to concurrently ensure an optimal force transmission between the elements and to concurrently achieve the desired mobility. Here, the corresponding contour, at least in sections, is shaped accordingly, especially as a function of the different body planes.

Moreover, it has proven to be especially advantageous for the intermediate element to have a cross sectional surface that differs in sections in the direction of its annular central axis and that interacts with a correspondingly shaped contour so that a form-fit connection between the intermediate element and the outer elements allows torsional moments to take place. For example, constrictions can be provided in sections for this purpose. The diameter of the ring cross sectional surface can be modulated along the ring so that, even in the case of a ring that has a circular shape as seen from above, a rotational movement of the ring between the plate-shaped outer elements can be ruled out.

For example, for this purpose, the cross sectional surface in the sagittal plane, in the frontal plane and/or in the transversal plane of the patient can be widened in sections.

Fundamentally, the material properties can be selected as a function of the particular requirements. In actual practice, an especially advantageous configuration is one in which the intermediate element is made, at least in sections, of a polymer, especially polyethylene, so that it has very little susceptibility to wear while concurrently having high toughness and a limited elastic deformability.

Moreover, an especially reliable connection of the intervertebral disk will provide the elements with anchoring pins or anchoring elements that serve for anchoring in the bone on the sides facing the vertebral bodies and, during the implantation, these elements anchor themselves into the vertebral bodies.

Here, in an advantageous manner, the elements with their anchoring pins or anchoring elements are coated with titanium or other biocompatible materials on their side facing the vertebral bodies, these materials allowing a direct connection to the bone.

BRIEF DESCRIPTION OF THE DRAWINGS

The invention allows various embodiments. In order to further elucidate the basic principle, one of them is shown in the drawing and will be described below. The drawing shows the following:

FIG. 1 a sectional side view of an artificial intervertebral disk according to the invention;

FIG. 2 a top view of various intermediate elements for an artificial intervertebral disk according to the invention;

FIG. 3 various cross sectional shapes of the intermediate elements shown in FIG. 2;

FIG. 4 merely a section of an enlarged side view of an intermediate element shown in FIG. 2;

DETAILED DESCRIPTION

Figure 5:
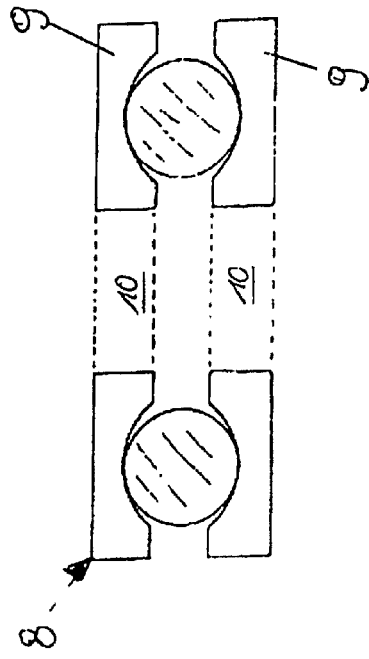
FIG. 5 another artificial intervertebral disk according to the invention in a sectional side view.

FIG. 1 shows a sectional side view of an artificial intervertebral disk 1 according to the invention, by means of which two adjacent vertebral bodies (not shown here) of a patient are joined to each other in an articulated manner. The artificial intervertebral disk 1 has an intermediate element 2 configured as an elastic ring that is inserted into a contour 3 of two outer elements 4 that are made, for example, of metal plates. The outer elements 4 are joined to the bones of the vertebral bodies by means of anchoring pins 5, especially titanium anchors, which are generally known from the field of hip prostheses. The radius D of the concave contour 3 has an oversize with respect to the diameter d of a circular cross sectional surface of the intermediate element 2, so that a compression of the intermediate element 2 stemming especially from movement by the patient allows a defined deformation.

FIG. 2 shows a top view of various possible shapes of the intermediate element 2 of the artificial intervertebral disk 1 according to the invention and each of these intermediate elements 2 has an annular closed basic shape. Shown by way of an example are intermediate elements 2a, 2b, 2c with a circular, oval or kidney-shaped basic shape. By the same token, of course, these basic shapes can also be provided with intermediate elements without cutouts (not shown here).

FIG. 3 shows by way of an example various cross sectional shapes of the intermediate element 2, which can be oval, circular or ogival on both sides. In the direction of the annular central axis 7 of the intermediate element 2 shown in FIG. 4, the cross sectional shape can also be configured differently in sections and can vary, for example, between the different cross sectional shapes depicted.

Such a varying cross sectional shape is depicted in greater detail in FIG. 4, which shows an enlarged side view of an intermediate element 2 shown in FIG. 2. One can see regular constrictions 6 of the circular cross sectional shape in the direction of the annular central axis 7 of the intermediate element 2 through which the occurring torsional moments can be transmitted due to a form-fit connection of the intermediate element 2 to the outer elements 4 shown in FIG. 1.

An embodiment of another artificial intervertebral disk 8 according to the invention that differs from that of FIG. 1 is shown in a sectional side view in FIG. 5. The intervertebral disk 8 has outer elements 9 configured as perforated plates having a central cutout 10 so as to improve the integration of the vertebral bodies 11 depicted in FIG. 6.

Figure 6:
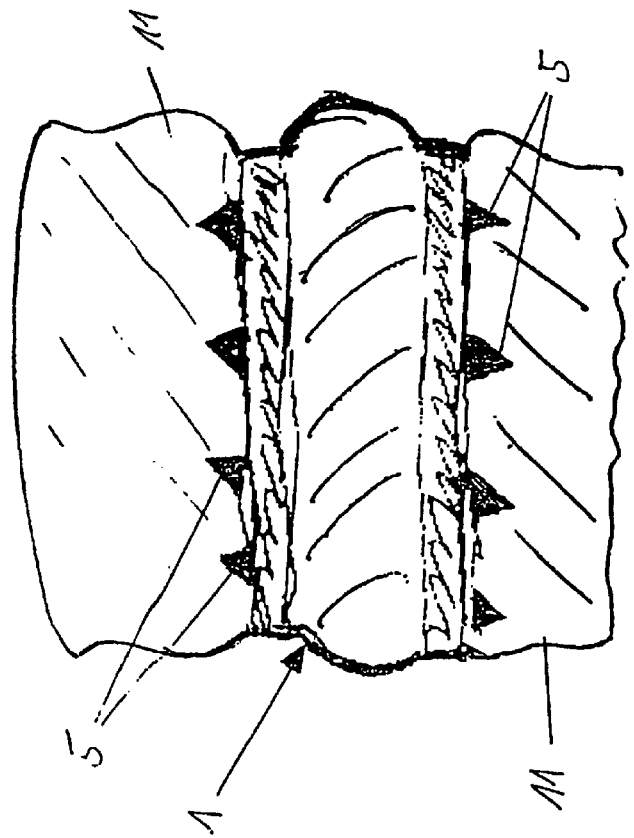
FIG. 6 the arrangement of the artificial intervertebral disk shown in FIG. 1 between two vertebral bodies of a vertebral column.

FIG. 6 shows an arrangement of the artificial intervertebral disk 1 shown in FIG. 1 between two vertebral bodies 11 of a vertebral column (not shown here). For purposes of anchoring in the vertebral bodies 11, the outsides of the intervertebral disk 1 facing the vertebral bodies 11 are provided with anchoring pins 5 that, during the implantation, anchor themselves in the vertebral bodies 11. A biocompatible coating on the sides facing the vertebral bodies 11 allows a direct connection to the bone.

The invention claimed is:

1. An artificial intervertebral disk insertable between two adjacent vertebral bodies of a patient, the artificial intervertebral disk comprising:
two outer elements, each associated with one of the two vertebral bodies disposed parallel to a first plane; and
an intermediate element having an annular closed shape and oval or circular cross-section in a second plane perpendicular to the first plane, at least in sections, in an uncompressed state of the intermediate element, wherein the intermediate element joins the two outer elements in a restricted, articulated manner such that torsional moments and shear forces are transmittable, wherein each of the two outer elements have an annular recess with a concave contour and is joined in a form-fitting manner to the intermediate element at the recess, and wherein the contour is oversized relative to the intermediate element such that a radius of the contour is greater than a radius of the intermediate element and a compression of the intermediate element allows a defined deformation of the intermediate element.

2. The intervertebral disk as recited in claim 1, wherein the contour has a friction-optimized surface texture.

3. The intervertebral disk as recited in claim 1, wherein the contour has a surface texture that increases the friction, at least in sections, so as to create a frictional connection between the two elements and the intermediate element at the sections.

4. The intervertebral disk as recited in claim 1, wherein the compression stems from a movement by the patient.

5. The intervertebral disk as recited in claim 1, wherein the intermediate element defines an annular central axis and has differing cross sections in a direction of the central axis and wherein the contour is correspondingly shaped.

6. The intervertebral disk as recited in claim 1, wherein a cross section of the intermediate element is widened in at least one of a sagittal plane, an intermediate plane, a frontal plane and a transversal plane of the patient.

7. The intervertebral disk as recited in claim 1, wherein the intermediate element is at least partially made of a polymer.

8. The intervertebral disk as recited in claim 7, wherein the polymer includes polyethylene.

9. The intervertebral disk as recited in claim 1, wherein the two outer elements include anchoring elements disposed on a side facing the vertebral bodies and configured to anchor the outer elements in the bone of the vertebral bodies.

10. The intervertebral disk as recited in claim 9, wherein the anchoring elements include anchoring pins.

11. The intervertebral disk as recited in claim 9, wherein the outer elements and anchoring elements are coated with a biocompatible material on the side facing the vertebral bodies.

12. The intervertebral disk as recited in claim 11, wherein the biocompatible material includes titanium.

* * * * *